United States Patent [19]

Miyazaki

[11] Patent Number: 4,784,117

[45] Date of Patent: Nov. 15, 1988

[54] ENDOSCOPE INSERTION ASSISTING DEVICE

[75] Inventor: Atsushi Miyazaki, Hachioji, Japan

[73] Assignee: Olympus Optical Co., Ltd., Tokyo, Japan

[21] Appl. No.: 14,907

[22] Filed: Feb. 13, 1987

[30] Foreign Application Priority Data

Feb. 14, 1986 [JP] Japan .................................. 61-30265
Feb. 17, 1986 [JP] Japan .................................. 61-32481
Apr. 23, 1986 [JP] Japan .......................... 61-61285[U]

[51] Int. Cl.⁴ ............................................. A61B 1/00
[52] U.S. Cl. ..................................................... 128/4
[58] Field of Search ....................... 128/4, 6; 138/120; 350/96.26

[56] References Cited

U.S. PATENT DOCUMENTS 3,805,770  4/1974  Okada ...................................... 128/4
4,630,649  12/1986  Oku ..................................... 128/4 X
4,696,544   9/1987  Costella ............................. 128/4 X

FOREIGN PATENT DOCUMENTS 2154335A  9/1985  United Kingdom .

*Primary Examiner*—William H. Grieb
*Attorney, Agent, or Firm*—Armstrong, Nikaido, Marmelstein & Kubovcik

[57] ABSTRACT

An endoscope insertion assisting device comprising a guide tube part provided with a hollow path through which an elongate endoscope insertion part can be inserted, a fitting part formed on the base side of this guide tube part and removably fitted with an endoscope operating part and a position adjusting mechanism varying at least one of the distance position along the longitudinal direction and the angular position around this longitudinal direction of this fitting part with respect to the guide tube part.

10 Claims, 10 Drawing Sheets ing device.

ENDOSCOPE INSERTION ASSISTING DEVICE

FIELD OF THE INVENTION AND RELATED ART STATEMENT

This invention relates to an endoscope insertion assisting device to be used to assist the insertion of an endoscope.

Recently, there has come to be extensively used an endoscope which can have the elongate insertion part inserted into a body cavity or pipe cavity to observe the interior of the body cavity or pipe cavity and to diagnose an affected part or to inspect a damage.

The insertion part of the above mentioned endoscope is made flexible so as to be able to be inserted through a bent insertion course. However, due to this flexibility, the direction of the tip side will not be fixed with respect to the holding side and it will be difficult to introduce the tip side in an object direction in some case.

Therefore, for example, in the specification of GB No. 2,154,335A, there is disclosed a prior art example of an endoscope insertion assisting device provided with a hollow shaft through which an endoscope can be passed so that the insertion part of the endoscope can be projected out of the opening on the tip side of this shaft and provided on the holding side with a curving operation means.

However, in the above mentioned prior art example, there has been a problem that, though the direction of projecting the tip side of the insertion part can be controlled, as the entire length is not variable, the position of projecting the insertion part will be substantially determined and therefore it will be difficult to more minutely control the direction.

Also, in the above mentioned prior art example, in the case of changing the visual field direction or in the case of photographing by fitting a photographing device and properly adjusting the vertical direction, generally, as the operating part of the endoscope is of a form different from a cylindrical or conical form which would be easy to rotate, the endoscope will not be able to be rotated independently of the assisting device.

Therefore, in order to set the endoscope in a direction adapted to observation or photographing, the endoscope must be pulled out by a proper length, then rotated to be set in a proper direction and then again refitted and thus there has been a defect that the operability is low.

Further, there have been defects that, in the above mentioned prior art example, the length of the projected part of the endoscope insertion part after the endoscope is inserted through this prior art example to be projected is so long that the insertion part will be deviated from the object direction by its own weight and flexibility, it will be difficult to lead the insertion part to the object position, the insertion part will unstably move due to the deflection, the observation visual field will move unexpectedly and the observation will be difficult.

OBJECTS AND SUMMARY OF THE INVENTION

An object of the present invention is to provide an endoscope insertion assisting device whereby the tip side of an endoscope insertion part can be easily guided to an object position or the like.

Another object of the present invention is to provide an endoscope insertion assisting device whereby the tip side of an endoscope insertion part can be minutely controlled.

Further, another object of the present invention is to provide an endoscope insertion assisting device whereby an endoscope can be rotated or the like independently of the assisting device side to improve operability.

In the present invention, an endoscope insertion assisting device is formed by comprising a flexible guide tube part provided with a hollow path through which an endoscope insertion part can be inserted, a fitting part formed on the base side of this guide tube part and capable of being fitted with an endoscope operating part and a position adjusting mechanism capable of varying the distance or angle of the fitting part with respect to the guide tube part.

BRIEF DESCRIPTION OF THE DRAWINGS

FIG. 1 is a sectioned view showing the periphery of an endoscope fitting part in the assisting device of the first embodiment.

FIG. 2 is a side view showing the entirety of the first embodiment.

FIG. 3 is a sectioned view on line A-A' in FIG. 1.

FIG. 4 is a sectioned view on line B-B' in FIG. 1.

FIG. 5 is a sectioned view on line C-C' in FIG. 1.

FIG. 6 is a sectioned view on line D-D' in FIG. 1.

FIG. 7 is an exemplary view showing a using example.

FIGS. 8 to 15 relate to the second embodiment of the present invention.

FIG. 8 is a sectioned view showing the structure of the second embodiment.

FIG. 9 is a perspective view showing the appearance of the second embodiment as fitted with a holding device.

FIG. 10 is a sectioned view on line E-E' in FIG. 8.

FIG. 11 is a sectioned view on line F-F' in FIG. 8.

FIG. 12 is a side view showing a part of a scope holding part as made short.

FIG. 13 is a side view showing a fitting plate for fixing the holding device.

FIG. 14 is a magnified perspective view showing a hollow elastic disk used for the fitting plate in FIG. 13.

DETAILED DESCRIPTION OF PREFERRED EMBODIMENT

Figure 1:
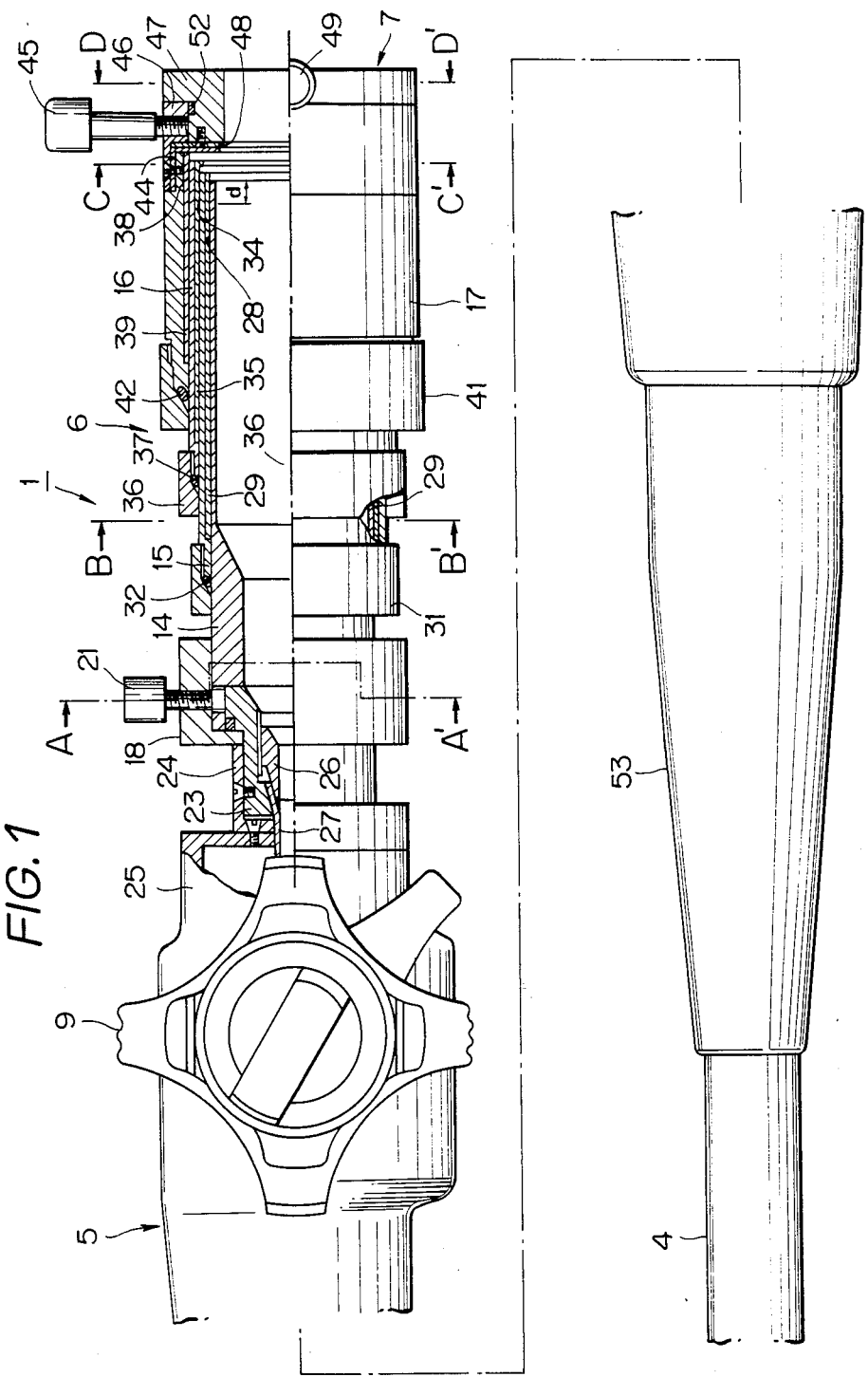
FIGS. 1 to 7 relate to the first embodiment of the present invention.
Figure 2:
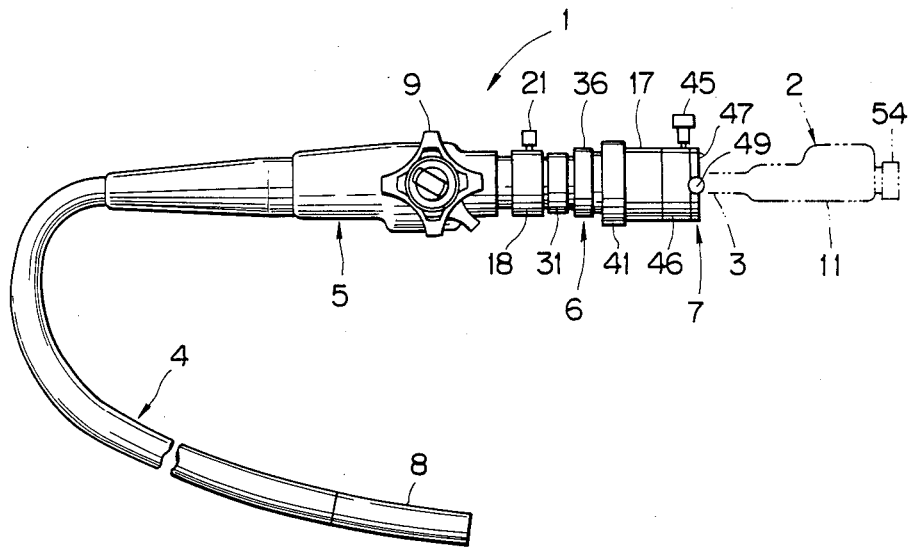

An endoscope insertion assisting device 1 of the first embodiment is formed of an elongate flexible guide tube part 4 provided with a hollow path through which an insertion part 3 of an endoscope 2 can be inserted, a wide guide tube operating part 5 provided as connected to the rear end side of this guide tube part and an endoscope holding part 6 formed at the rear end of this guide tube operating part 5 and extendable to hold the endoscope 2. An endoscope fitting part 7 to which the endoscope 2 can be fitted is formed in this endoscope holding part.

Many articulated frames not illustrated are connected in a longitudinal row to form a curvable part 8 on the front end side of the above mentioned guide tube part 4. These articulated frames are connected through wires inserted through the guide tube part 4 with a mechanism for pulling and relaxing the wires within the operating part 5 so that, by rotating a curving operation knob 9 provided on the outer surface of the operating part 5, the curvable part 8 can be curved vertically or horizontally.

The above mentioned holding part 6 formed on the front part side of the endoscope fitting part 7 to which the operating part 11 of the above mentioned endoscope 2 can be removably fitted is of such structure as is shown, for example, in FIG. 1.

In this holding part 6, by sliding, for example, four pipes 14, 15, 16 and 17, the entire length of the holding part 6 can be varied and the distance of the endoscope fitting part 7 to which the endoscope 2 is fitted can be varied with respect to the operating part 5.

Figure 3:
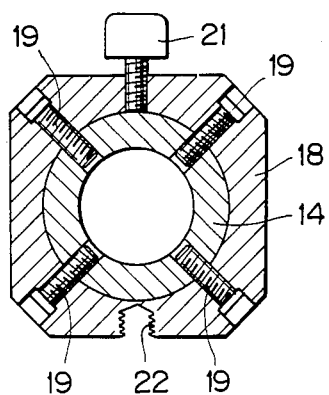

The first pipe 14 is externally fitted with a holding part retaining member 18 on the outer periphery at the front end made thicker. In this retaining member 18, as shown in FIG. 3, screws 19 are screwed respectively into screw holes provided in four places and are engaged respectively with the screw holes on the pipe 14 side so that the pipe 14 can be fixed to the retaining member 18 so as not to rotate. When a rotation stopping grip 21 fitted by screwing to this retaining member 18 presses an outside pressing member 23 on the outer peripheral surface, the rotation on the tip side forward of the pressing member 23 of the assisting device 1 will be able to be controlled. This retaining member 18 is provided with a screw hole 22 for fitting a tripod or the like on the side, for example, reverse to the grip 21 so that the holding part 6 can be fixed with the tripod or the like.

The above mentioned retaining member 18 projects on the front end side diametrally inward so as to externally fit an outside pressing member 23 inside the front end of the pipe 14 and contacts on the front surface with the rear end surface of a jointing member 24 so as to be prevented from being removed. This jointing member 24 is fixed by a screw or the like to the rear end of a body 25 of the operating part 5.

The above mentioned outside pressing member 23 has a female screw formed on the inner peripheral surface and an inside pressing member 26 provided with a male screw to be screwed with this female screw is screwed with the outside pressing member 23. A flexible guide tube 27 is fixed as pressed between the tapered surfaces of both pressing members 23 and 26. The inside diameter of this guide tube 27 is made somewhat larger than the outside diameter of the insertion part 3 of the endoscope 2 to be inserted through the guide tube 27. An O-ring is fitted in the part steppedly made larger in the diameter of the outside pressing member 23.

Figure 4:
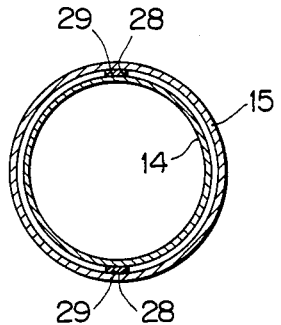

The above mentioned first pipe 14 is fitted into the second pipe 15 so as to be slidable in the longitudinal direction (forward and rearward). So as to be movable in the longitudinal direction without rotating accidentally in such case, the first pipe 14 is made a little larger in the diameter for a proper length d near the rear end (See FIG. 1) and is provided with key grooves 28 above and below as shown in FIG. 4. Square keys 29 fitted by screws or the like in the longitudinal direction (forward and rearward) on the inner wall of the second pipe 15 are engaged with the respective key grooves 28.

The above mentioned second pipe 15 has a male screw formed on the outer periphery at the front end so that a retaining ring 31 can be screwed with the second pipe 15. An O-ring 32 is fitted on the tapered surface inside this retaining ring 31 so as to increase the screwed amount of the retaining ring 31, to thereby prevent the first pipe 14 and second pipe 15 by the friction of the O-ring 32 from sliding between them and to be able to fix them in any desired length position.

The same means is formed also for the above mentioned second pipe 15 and third pipe 16.

That is to say, the second pipe 15 is made larger in the outside diameter in the part near the rear end and is provided with key grooves 34. Square keys 35 fitted to the third pipe 16 are engaged respectively with the key grooves 34 so that the second pipe 15 can slide forward and rearward as fitted in the third pipe. The third pipe 16 has a male screw formed on the outer periphery at the front end and an O-ring 37 fitted inside the tapered inner peripheral surface is pressed by a retaining ring 36 to form a clamping means which can fix the second pipe 15 and third pipe 16 so as not to move forward and rearward.

Figure 5:
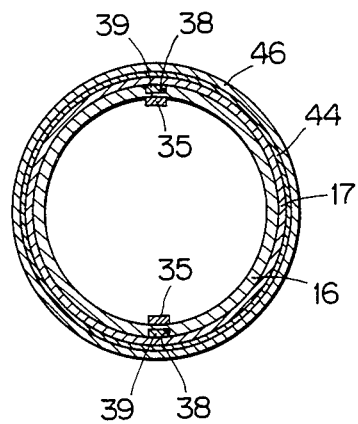

As shown in FIG. 5, the third pipe 16 is also made larger in the diameter on the outer periphery at the rear end and is provided with key grooves 38 so as to be slidable forward and rearward with square keys 39 of the fourth pipe fitted respectively in the key grooves 38. Also, the fourth pipe 17 has a male screw formed on the outer periphery at the front end so that the retaining ring 41 can be screwed with it and that the third pipe 16 and fourth pipe 17 can be clamped with each other by pressing an O-ring 42 fitted on the inner periphery of the retaining ring 41.

A fitting part 7 provided with a rotary mechanism so as to be able to rotatably fit the endoscope 2 is formed on the rear end side of the above mentioned fourth pipe 17.

The fourth pipe 17 is incised on the outer periphery at the rear end and a ring 46 provided with a rotation stopping grip 45 by fitting a stopper 44 is fixed by a screw or the like in the thin part on the front end side. This ring 46 projects on the rear end side more rearward than the fourth pipe 17 and is externally fitted in a recess formed on the outer periphery at the front end of the scope holding member 47. This scope holding member 47 is fixed on the front end surface with a hollow pressing disk 48 through screws or the like. This pressing disk 48 is fitted so as to hold the front and rear surfaces of the ring 46 provided with the grip 5 to project with the scope holding member 47 and the scope holding member 47 side holding the endoscope 2 fitted to this ring 46 is made rotatable. By the way, the pressing disk 48 prevents the scope holding member 47 from escaping rearward. By rotating the grip 45 provided to project by engaging the screwed part with the screw hole in the ring 46 to set the inside tip of the screw part so as to press the the scope holding member 47 on the outer surface, the scope holding member 47 can be clamped so as not to rotate and the direction of the fitted endoscope 2 can be set in any position. That is to say, by varying the entire length of the holding part 6 with the above mentioned pipes 14, 15, 16 and 17, the distance position of the fitting part 7 to which the endoscope 2 is fitted and held can be variably adjusted with respect to the operating part 5 (or the guide tube part 4) side of the assisting device 1 and the direction (angular position) of the endoscope 2 fitted to the fitting part 7 can be variably adjusted by the above mentioned rotary mechanism and rotation stopping mechanism. The formation of such position adjusting mechanism or means is a feature of the first embodiment.

Figure 6:
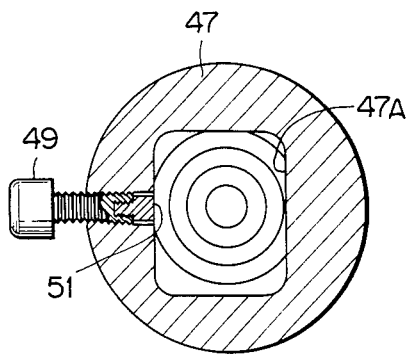

Now, as shown in FIG. 6, the above mentioned scope holding member 47 is provided with a substantially rectangular inner wall surface 47A corresponding to the contour of the operating part 11 of the endoscope 2 so as to be able to be fitted without a backlash.

The screw part screwed in the screw hole in the scope holding member 47 in the scope pressing grip 49 provided to project in the scope holding member 47 is projected in the inside direction and is pressed through a pressing protecting member 51 so as to press the operating part 11 of the endoscope 2 on the side to be able to fix the endoscope 2. By the way, an O-ring 52 is fitted between the scope holding member 47 and the ring 46 provided with the grip 45 to project so as to have a proper friction force.

Now, the front side of the operating part 5 of the above mentioned assisting device is connected with the rear end of the guide tube part 4 protected by a tapered bend preventing member 53.

The operation of the thus formed first embodiment shall be explained in the following.

Figure 7:
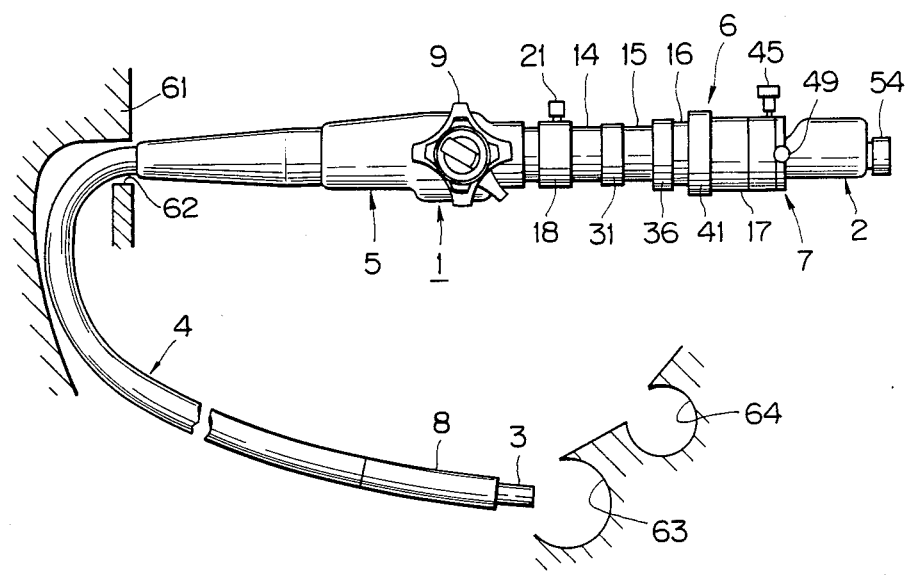

In the case of inspecting the interior of an engine, boiler or chemical plant by inserting the insertion part 3 of the endoscope 2 on the tip side into the assisting device 1 of the first embodiment, it shall be considered to inspect the inner wall surfaces of two recesses 63 and 64 in the depths of an inserting port part 62 of an object 61 to be inspected as shown, for example, in FIG. 7.

The endoscope 2 is fixed to the fitting part 7 so as to be able to observe the first recess 63 without deviating unstably. However, unless the length of the holding part 6 is variable, the inserted endoscope insertion part 3 will project at the tip too forward to be adapted to the observation of the position to be inspected in some case. However, in this first embodiment, by loosening at least one of the retaining rings 31, 36 and 41, the length by the pipes 14, 15, 16 and 17 can be varied. Therefore, as shown, for example, in FIG. 7, a proper length is set, then, by fastening the retaining rings 31, 36 and 41, the entire length of the assisting device 1 is fixed at a proper length and the opening at the tip of this assisting device 1 is directed to a position to be inspected. If the insertion part 3 is projected at the tip in this state, the observation will be able to be made by shortening the length of the projecting part of the insertion part 3. Therefore, the problem can be solved that the insertion part 3 deflects on the tip side to be difficult to lead to the object position, and it can be prevented that the insertion part becomes unstable to be likely to vibrate and the operability in the case of an observation can be improved. That is to say, the length of the assisting device can be adjusted to be a length adapted to the length of the insertion part 3 of the endoscope 2 used in practice or the distance to the inspected position and can be minutely controlled.

The visual field direction may be set in any direction desired by the user as in the following.

When the grip 45 of the ring 46 is loosened, the scope holding member 47 will become rotatable independently of the ring 46 side, that is, the respective pipes 14, 15, 16 and 17 to which this ring 46 is connected and the operating part 5. Therefore, the endoscope 2 together with this scope holding member 47 will become rotatable. Therefore, when the endoscope 2 is rotated to be set in a direction adapted to the observation and then the grip 45 is fastened, the endoscope will be able to be set in the direction adapted to the observation. Thus, it can be set in the direction adapted to the observation with a simple operation and therefore the operability can be greatly improved.

In the case of photographing with a photographing device fitted to an eyepiece part 54 of the endoscope 2, by utilizing the tripod fitting screw hole provided in the retaining member 18, the assisting device 1 can be prevented from moving to cause deflection in photographing. Even in case the photographing visual field direction is improper, by the grip 45, the photographing device will be able to be simply reset and diagnosing or inspecting photographing will be able to be completed within a short time.

By the way, in the above mentioned first embodiment, as a sliding mechanism, for example, for the first pipe 14 and second pipe 15, a key may be fitted to the rear end of the first pipe 14 and, on the other hand, a key groove may be provided on the inner wall side of the second pipe 15.

Figure 8:
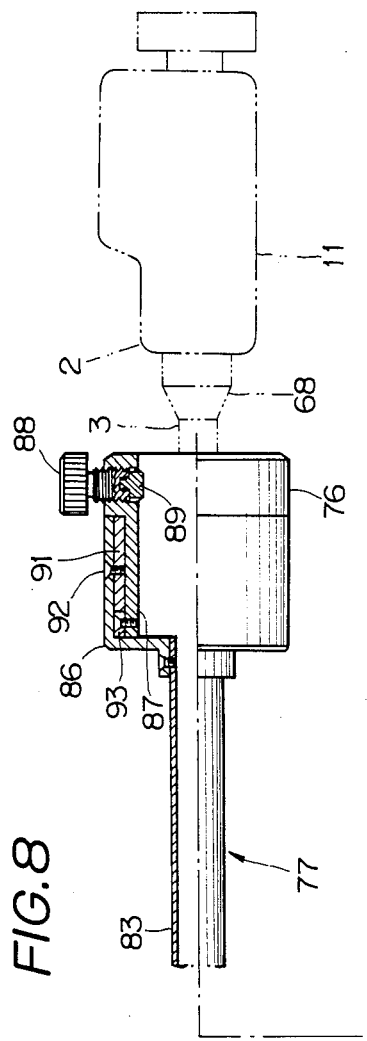
Figure 8:
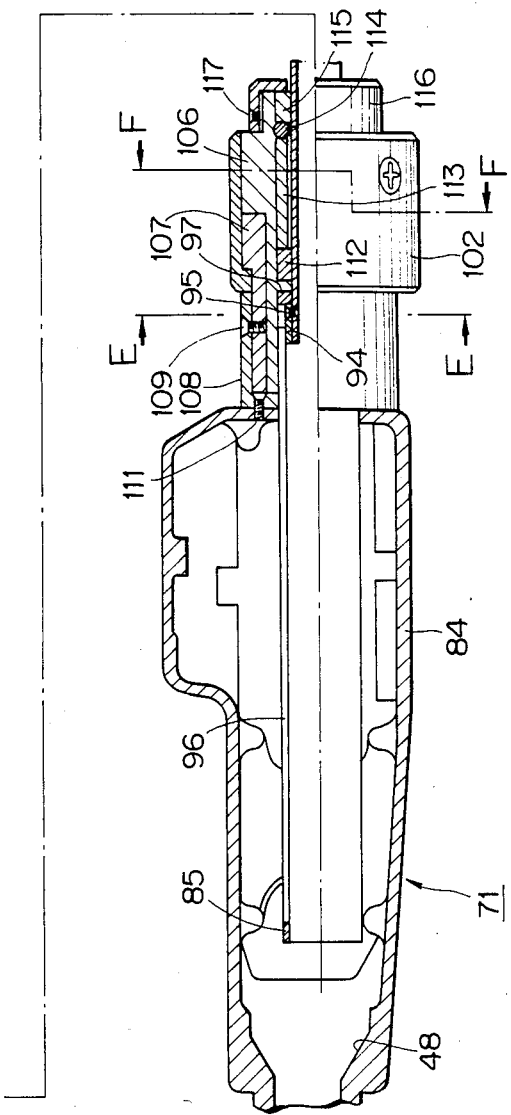
Figure 9:
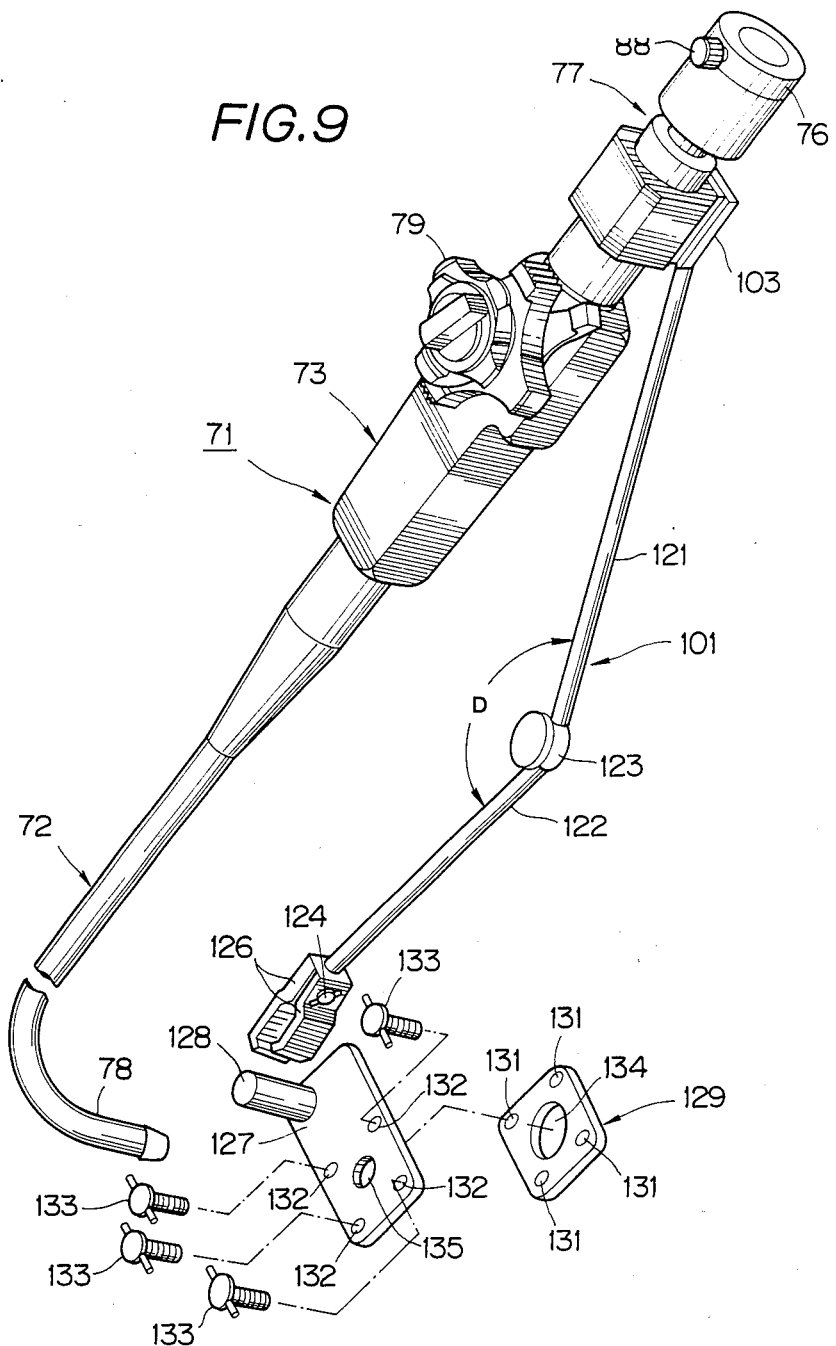

As shown in FIG. 9, an endoscope insertion assisting device 71 of the second embodiment is formed of an elongate hollow guide tube part 72, a wide guide tube operating part 73 provided as connected to the rear end side of this guide tube part 72 and an endoscope holding part (scope holding part) 77 formed on the rear end side of this guide tube operating part 73 and provided at the end with an endoscope fitting part (scope fitting part) 76 fitted with an endoscope operating part (scope operating part) 11 of the endoscope 2 indicated by the two-point chain lines in FIG. 8.

Many articulated frames not illustrated are connected in a longitudinal row to form a curvable part 78 on the front end side of the above mentioned guide tube part 72. These articulated frames are connected through wires inserted through the guide tube part with a mechanism for pulling and relaxing the wires within the operating part 73 so that, by rotating a curving operation knob 79 provided on the outer surface of the operating part 73, the curvable part 78 can be curved vertically or horizontally and that the endoscope insertion part 3 inserted through the hollow path within the guide tube 72 can be bent on the tip side and can be led toward the object position.

The above mentioned endoscope holding part (scope holding part) 77 is of such structure as is shown, for example, in FIG. 8.

Figure 12:
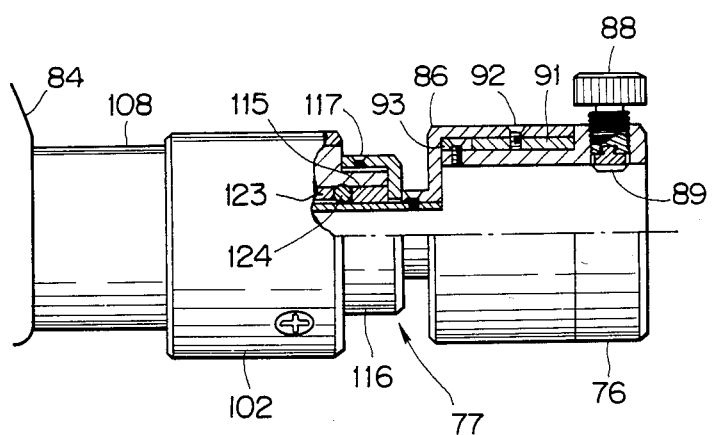

A cylindrical elongate hollow sliding pipe 83 is of an inside diameter which can be inserted through the endoscope insertion part 3 and of an outside diameter which can slide to move forward and rearward within a guide pipe 85 provided within an operating part body 84. Depending on the amount contained within this guide pipe 85 of the sliding pipe 83, the sliding pipe 83 can project rearward of the operating part 73 (as in FIG. 8) or can be (substantially) contained within the operating part 73 (as in FIGS. 9 and 12) to make the scope holding part 77 telescopically extendable. A scope presser 86 secured with a screw to the outer periphery of the front part of the scope fitting part 76 is secured with a screw to the rear end of this sliding pipe 83.

In the above mentioned scope fitting part 76, a fitting inner wall surface 87 of a form in which the scope operating part 11 can be fitted is formed so that the scope operating part 11 can be pressed and fixed with a scope retaining screw 88. By the way, this scope retaining screw 88 is fitted at the tip with a protective member 89 so as to be able to be fixed without hurting the outer surface of the scope operating part 11 when the screw 88 is pressed.

The above mentioned scope fitting part 76 is steppedly made thinner on the outer periphery on the front side and a ring-shaped rotation presser 91 is externally fitted on the outer peripheral surface and is secured with a screw 92 to the above mentioned scope presser 86 which is further externally fitted. The scope fitting part 76 is made rotatable together with the endoscope 2 fitted to this scope fitting part 76 with respect to this rotation presser 91. By the way, a ring-shaped sliding preventer (removal preventer) 93 is secured with a screw to the outer periphery in the front part of this scope fitting part 76.

Figure 10:
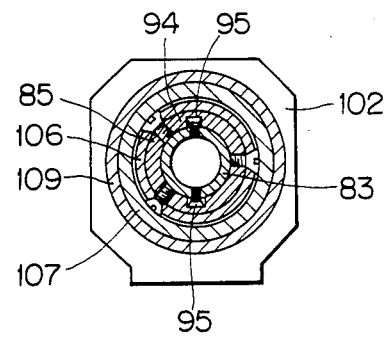

As shown in FIG. 10, a stopper 94 is provided in the front part of the above mentioned sliding pipe 83 and guide screws 95 are provided to project respectively in two places opposed to each other on the outer periphery of the stopper 94 so as to move in rotation stopping grooves 96 in the guide pipe 85.

An assisting device fitting part 102 which can removably fit this assisting device 71 to a holding device 101 shown in FIG. 9 is formed at the rear end of the above mentioned operating part body 84.

Figure 11:
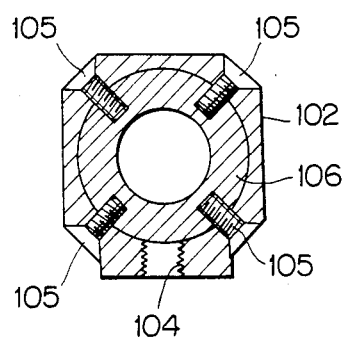

The above mentioned assisting device fitting part 102 is provided with a screw hole 104 making it possible to fit a fitting plate 103 of the above mentioned holding device 101 or a tripod (See FIG. 11).

As shown in FIG. 11, this assisting device fitting part 102 is fixed to a fixing member 106 inside it with four screws 105. A rotary member 107 is rotatably externally fitted to the outer periphery in the front part steppedly made smaller in the diameter of this fixing member 106 and is secured with a screw 109 to a connecting member 108.

This connecting member 108 is connected with the operating part body 84 through a screw 111.

The above mentioned rotary member 107 and connecting member 108 are rotatable with respect to the assisting device fitting part 102 and fixing member 106.

The above mentioned guide pipe 85 is fitted at the rear end on the inner periphery in the front part of the above mentioned fixing member 106 and is secured with three screws as shown in FIG. 10. Further, a ring-shaped slider 112, spacer 113, O-ring 114 and slider 115 are fitted on the inner periphery on the rear part side of a projection in the inside diameter direction of this fixing member 106. On the other hand, a male screw part is formed on the outer periphery at the rear end of the above mentioned fixing member 106 and is secured with a pressing member 116. By rotating this pressing member 116 to vary the screwed amount, the slider 115 can be moved to adjust the projected amount in the inside direction by the pressed deformation of the O-ring 114. The friction force with the sliding pipe 83 which can move in the longitudinal direction in sliding contact with this O-ring 114 can be varied by the deformation of this O-ring 114. After a proper friction force state is set, the friction state can be held with a pressing screw 117.

Grease is applied to the surface of contact of the rotary member 107 and fixed member 106 with each other to make the rotation smooth.

A tapered incised surface 118 is provided on the front part side of the operating part body 84 so that the inserted scope insertion part 3 can be led to pass through the center of the guide tube part 72.

Now, the holding device 101 to which the assisting device 71 is to be fitted is of such structure as is shown, for example, in FIG. 9.

One arm 121 of a pair of arms 121 and 122 is provided to project from a fitting plate 103 removably fitted with screws to the assisting device fitting part 102 of the assisting device 71 and is connected at the other end to the other arm 122 through a bendable bending part 123 which can vary the angle D between both arms 121 and 122.

Figure 13:
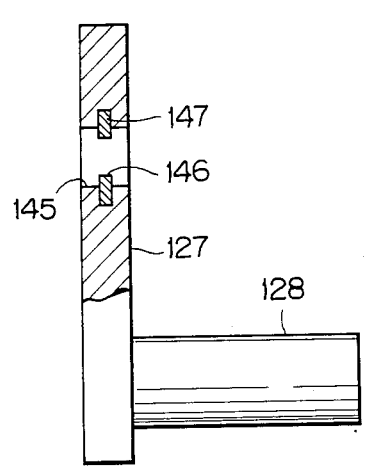

This arm 122 is fitted at the other end with a pair of gripping pieces 126 opened and closed with a screw 124. As shown in FIGS. 9 or 13, these gripping pieces 126 can be fixed as gripping a fitting bar 128 provided to project on a fitting plate 127 as shown in FIG. 13. By gripping this fitting bar 128, the assisting device 71 and the endoscope 2 fitted to this assisting device 71 can be held by the fitting plate 127 through this holding device 101 without any backlash.

The above mentioned fitting plate 127 is provided with screw holes 132 communicating with respective screw holes in a fitting part 129 as in close contact with the fitting part 129, for example, of a jet engine to be observed so that the fitting plate 127 may be fixed to the fitting part of the jet engine by the respective fixing screws 133.

This fitting plate 127 is provided with a through hole 135 which communicates with an observing hole 134 provided in the fitting part 129 of the above mentioned jet engine and which is somewhat larger than the outside diameter of the guide tube 72 of the assisting device 71.

In this through hole 135, as shown in FIG. 13, a ring-shaped recess is formed near the middle in the thickness direction and a hollow elastic disk 147 provided with a through hole 136 of an inside diameter making the guide tube part 72 insertable is fitted in this recess.

A scope fitting part 76 making it possible to rotatably fit endoscope 2 is made short in the length by using a short break preventing member 138 for the endoscope 2 (indicated by the two-point chain lines in FIG. 8) fitted to this scope fitting part 76. In the case of the endoscope of a long break preventing member, the long break preventing member may be removed and such short one as is shown in FIG. 8 may be fitted in using the endoscope.

An example of using the assisting device 71 of the thus formed second embodiment shall be explained in the following.

In the case of inspecting the interior of a jet engine, the fitting plate 127 is closely fitted and the respective screws 133 are screwed to firmly fix the fitting plate 127 to the fitting part 129.

The holding device 101 can be held by strongly gripping the fitting bar 128 of this fitting plate 127 with the gripping pieces 126. The fitting plate 123 at the end of the arm 121 of this holding device 101 is fitted to the assisting device fitting part 102 of the assisting device 71 so that the assisting device 71 and the endoscope 2 fitted to the assisting device may be held without any backlash. Thus, the guide tube part 72 of the assisting device 71 fitted to this endoscope 2 can be introduced on the tip side into the jet engine through the through hole 135 in the fitting plate 127 and the observing hole 134 on the jet engine side. In this case, by connecting a light guide cable not illustrated of the endoscope 2 to the light source device, an illuminating light can be emitted out of the illuminating window at the tip of the scope insertion part 3 and the interior of the jet engine illuminated by this illuminating light can be observed with the observing optical system. For example, in case the tip is too far away from the position to be observed, if the angle D formed by both arms 121 and 122 is made smaller by operating the bending part 123 of the holding device 101, the tip can be brought nearer for the observation. In the case of changing the observing or inspecting place, the distance from the position of the assisting device fitting part 102 of the assisting device 71 to the fitting plate 127 or fitting part 129 can be varied by varying the angle D between both arms 121 and 122 by rotating the bending part and therefore the observing or inspecting place can be simply changed. Also, as the through hole 135 in the above mentioned fitting plate 127 is provided with the elastic disk 137 having an elasticity, the guide tube part 72 can be held without any backlash and can be inserted without any difficulty.

On the other hand, even in the case of using a holding device in which the above mentioned arm length or angle can not be varied or using a tripod, according to the second embodiment, the length of the scope holding part 77 can be varied by moving the sliding pipe 83 and therefore the position (observing distance) of the tip side of the scope insertion part 3 projecting out of the assisting device 71 can be varied. As the movement of the sliding pipe 83 in this case is set at a proper friction resistance by the O-ring 114, even if either of the sliding pipe 83 and scope fitting part 76 is moved and operated, it can be smoothly moved and set without sliding too much.

When the sliding pipe 83 is contracted (FIG. 12), the distance between the guide tube operating part 73 and the scope operating part 11 can be made short enough, such operation as of curving can be easily made and the operability can be improved.

Figure 14:
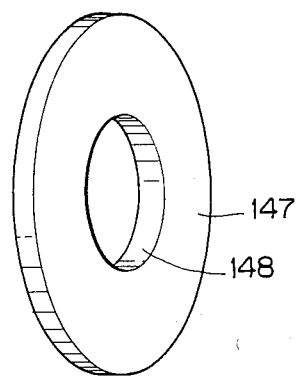

Now, the elastic disk to be fitted to the through hole 135 in the fitting plate 127 is not limited to be such as is shown in FIG. 14 but may be of such form as is shown in FIG. 15.

Figure 15A:
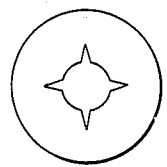
FIGS. 15a, 15b, 15c and 15d show front views of alternative hollow elastic disks usable in the fitting plate of FIG. 13.
Figure 15B:
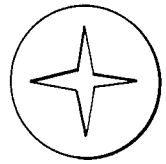
Figure 15C:
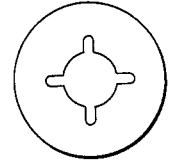
Figure 15D:
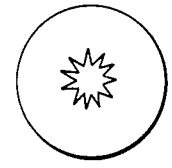

In the one shown in FIG. 15a, a circular inserting hole through which the guide tube part 72 is to be inserted is provided, for example, in four places with incisions. In the one shown in FIG. 15b, a cruciform incision is made. In FIG. 15c, the same incisions as in FIG. 15a are made but are rounded in the depths. In the one shown in FIG. 15d, many radial incisions are made.

Figure 16:
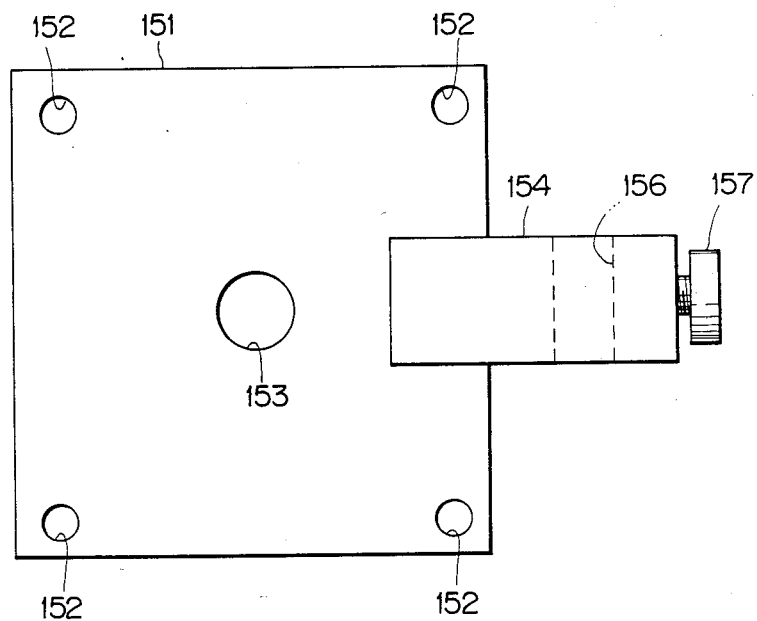
FIG. 16 is an elevation showing another embodiment of the fitting plate.
Figure 17:
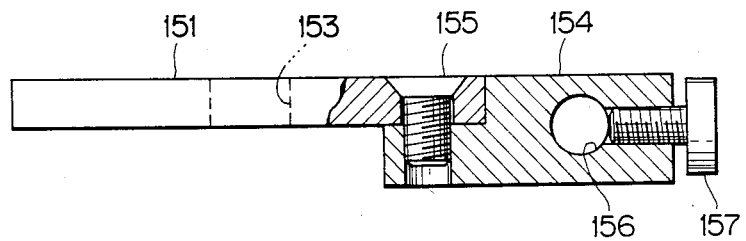
FIG. 17 is a sectioned view of FIG. 16.

Also, the fitting plate is not limited to be the one shown in FIG. 15 but may be of such form as is shown in FIGS. 16 or 17.

That is to say, a square fitting plate 151 is provided in the four corners with respective holes (or screw holes) 152 so as to be fixed with screws and in the center with a through hole 153 through which the guide tube part 72 can be inserted. Also, a fitting bar 154 is secured with a screw 155 in a direction parallel, for example, with the plate surface of this fitting plate 151 so as to project in a direction at right angles with the above mentioned through hole 153, is provided with a hole 156 through which, for example, the arm 122 can be passed and can be fixed with a screw 157 from the side.

Figure 18:
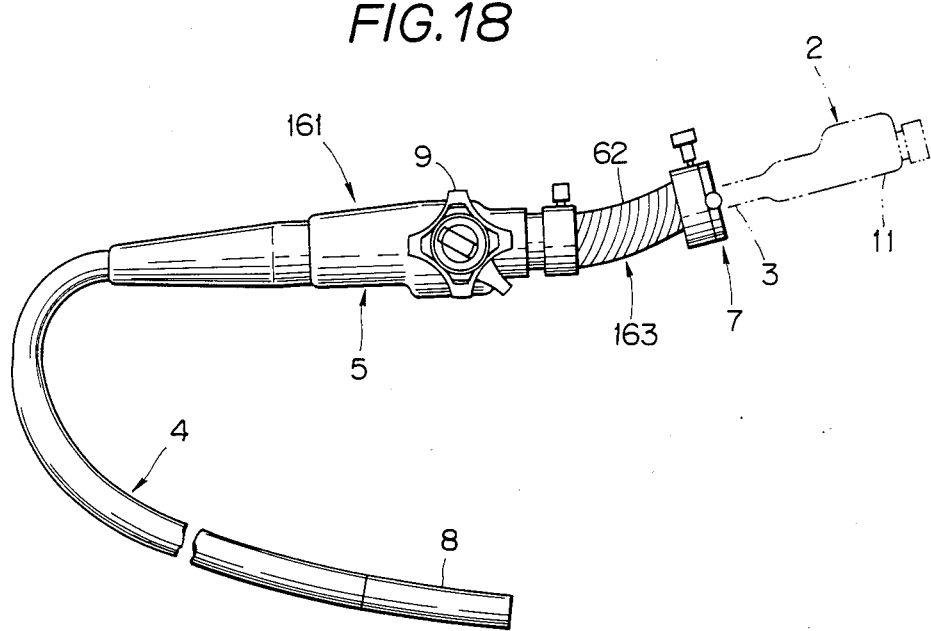
FIG. 18 is a side view showing the entirety of the third embodiment of the present invention.

FIG. 18 shows an essential part of the third embodiment of the present invention.

In the above mentioned first embodiment, the telescopically extendable holding part 6 is formed of the pipes 14, 15, 16 and 17, whereas, in this third embodiment, as illustrated, a bendable holding part 163 is formed of an interlocked type spiral tube 162 in an assisting device 161. The rotatably fittable part 7 is formed on the rear end side of this holding part 163.

The others are the same as in the above mentioned first embodiment.

Figure 19:
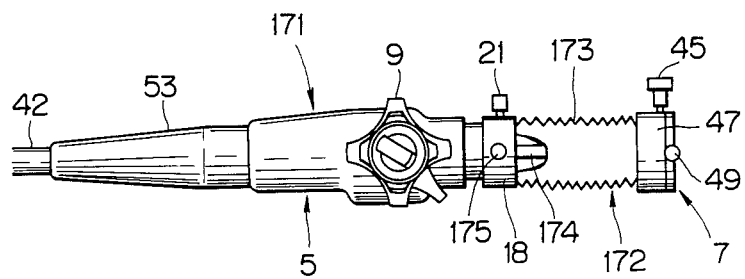
FIG. 19 is a side view showing a part of the fourth embodiment of the present invention.

FIG. 19 shows the fourth embodiment of the present invention.

In an assisting device 171 in this fourth embodiment, a holding part 172 is formed of a bellows 173. Within this bellows 173, for example, a guide bar 174 is projected forward out of the scope holding member 47 and passes through a guide hole not illustrated within the retaining member 18 so that the length of the holding part 172 to the scope holding member 47 can be varied. This guide bar 174 can be fixed, for example, by a grip 175 on the retaining member 18.

The operation and effects of this fourth embodiment are substantially the same as of the above mentioned first embodiment.

Figure 20:
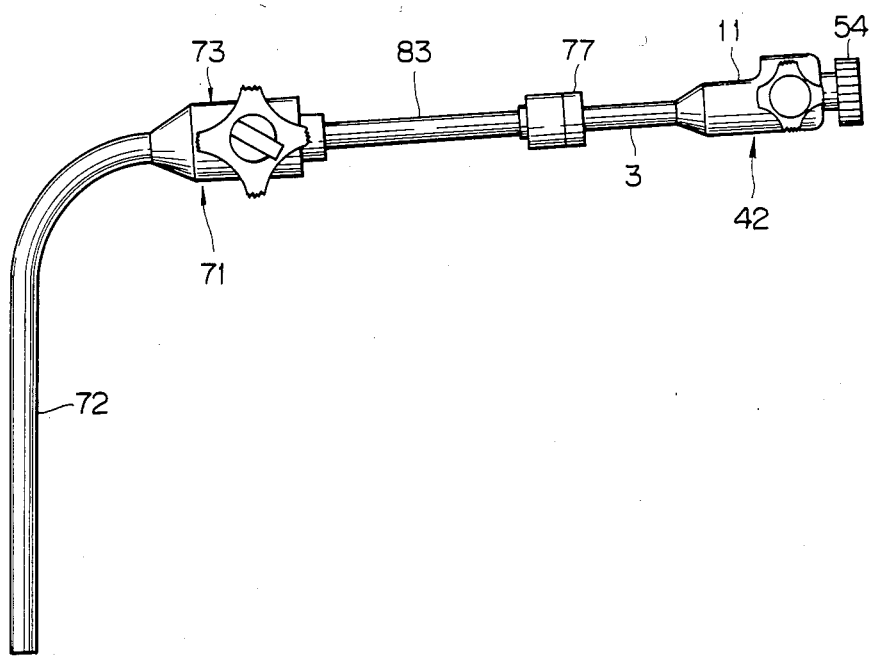
FIG. 20 is an explanatory view showing the manner of making it easy to insert the endoscope into the second embodiment by using an inserting bar.
Figure 20:
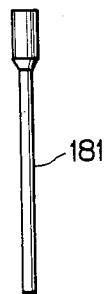

In the case of inserting the endoscope 2 into the assisting device 71, for example, of the second embodiment, when the tip part of the endoscope 2 catches on the guide tube part 72 or the like within the assisting device 71, as shown in FIG. 20, an insertion bar 181 of an insertable outside diameter may be inserted into the guide tube part 72 from the tip side of the guide tube part 72 so as to be in contact at the tip with the tip surface of the endoscope 2 and, in this state, the endoscope 2 may be pushed and inserted while pulling the insertion bar 181.

If the above mentioned insertion bar 181 is rigid or flexible nearly rigid, the insertion of the endoscope 2 will be able to be more effectively made.

The rotary mechanism on the endoscope fitting part 7 side to which the endoscope 2 is fitted (for example, between the ring 46 and scope holding member 47 in FIG. 1) and the rotary mechanism on the assisting device body side (operating part 5 side) (for example, between the fitting surfaces of the pipe 14 and retaining member 18 in FIG. 3) may be provided with clicking mechanisms so as to be able to be set at a high reproducibility for each rotation of an angle of several degrees.

The the rotation on the endoscope fitting part 7 and operating part 5 side may be electrically made by using a motor or the like.

In case the endoscope holding part 6 or the like is extendable, a mechanism by which it can be clicklocked in a predetermined extended position may be provided.

The guide tube part 4 is made curvable on the tip side in one place but can be made curvable in two places of the tip part and an intermediate position or the like.

The entire guide tube part 4 is made a soft guide tube part having a flexibility in the above mentioned embodiment but may be made partly rigid. Also, the entire guide tube part 4 may be made rigid in an extendable structure.

Now, for example, in the second embodiment, the holding part 77 is prevented by using a key and key groove from rotating. However, the present invention is not limited to it. The holding part may be of such structure rotatable at the time of the extending and contracting operation as of a tripod for cameras.

The mechanism for fixing the extending and contracting operation and rotating operation may be operated against a proper extending and contracting resistance and rotating resistance in a half fixed state.

By the way, the present invention is not limited to the above described embodiments, may be provided with an adjusting mechanism which can vary at least one of the distance position along the longitudinal direction and the angular position around the longitudinal direction in the endoscope 2 fitted to the fitting part and has a sufficient operability with only one adjusting mechanism depending on the use.

In the assisting device of the present invention, the guide tube operating part is formed at the rear end of the guide tube part. However, without providing the guide tube part operating part, the rear end part of the guide tube part may be made wider and the fitting part able to adjust the position may be provided.

What is claimed is:

1. An endoscope insertion assisting device comprising a guide tube part provided with a hollow path through which an elongated endoscope insertion part can be inserted, a fitting part formed on the base side of said guide tube part and removably fitted with an endoscope operating part formed on the base side of said endoscope insertion part and a position adjusting mechanism capable of varying the position of said fitting part with respect of said guide tube part.

2. An endoscope insertion assisting device comprising a guide tube part provided with a hollow path through which an elongated endoscope insertion part can be inserted, a guide tube operating part which is provided as connected to the base side of said guide tube part and in which a knob for curving a curvable part formed on the tip side of said guide tube part is formed, a fitting part formed in said guide tube operating part and removably fitted with an endoscope operating part formed on the base side of said endoscope insertion part and a position adjusting mechanism capable of varying the position of said fitting part with respect to said guide tube operating part.

3. An endoscope insertion assisting device according to claim 1 or 2 wherein said position adjusting mechanism is formed of a distance adjusting mechanism varying the distance position in the longitudinal direction.

4. An endoscope insertion assisting device according to claim 1 or 2 wherein said position adjusting mechanism is formed of an angular position adjusting mechanism varying the angular position of the endoscope fitted to said fitting part around the longitudinal direction.

5. An endoscope insertion assisting device according to claim 1 or 2 wherein said position adjusting mechanism is to vary the distance position in the longitudinal direction and the angular position around said longitudinal direction.

6. An endoscope insertion assisting device according to claim 3 wherein said position adjusting mechanism comprises a sliding pipe slidably connecting said guide tube part or guide tube operating part and said fitting part with each other and retaining members fixing the sliding of said sliding pipe.

7. An endoscope insertion assisting device according to claim 6 wherein said sliding pipe is a single pipe.

8. An endoscope insertion assisting device according to claim 6 wherein said sliding pipe consists of a plurality of pipes.

9. An endoscope insertion assisting device according to claim 3 wherein said position adjusting mechanism is formed of an extendable and contractable bellows member.

10. An endoscope insertion assisting device according to claim 3 wherein said position adjusting mechanism is formed of a bendable interlocked type spiral tube.

* * * * *